(12) United States Patent
Cole et al.

US006344314B2

(10) Patent No.: US 6,344,314 B2
(45) Date of Patent: Feb. 5, 2002

(54) DETERMINED DNA SEQUENCED DERIVED FROM A PAPILLOMAVIRUS GENOME, THEIR USES FOR IN VITRO DIAGNOSTIC PURPOSES AND THE PRODUCTION OF ANTIGENIC COMPOSITIONS

(75) Inventors: Stewart Cole, Chatillon sous Bagneux; Rolf E. Streeck, La Celle St-Cloud, both of (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/832,852

(22) Filed: Apr. 12, 2001

Related U.S. Application Data

(63) Continuation of application No. 09/577,493, filed on May 25, 2000, now Pat. No. 6,242,250, which is a continuation of application No. 09/330,076, filed on Jun. 11, 1999, now Pat. No. 6,107,086, and a continuation of application No. 08/789,781, filed on Jan. 28, 1997, now abandoned, which is a continuation of application No. 08/466,711, filed on Jun. 6, 1995, now Pat. No. 5,648,459, which is a division of application No. 08/222,569, filed on Mar. 25, 1994, now Pat. No. 5,554,538, which is a continuation of application No. 08/161,239, filed on Nov. 10, 1993, now abandoned, which is a continuation of application No. 08/032,694, filed on Mar. 17, 1993, now abandoned, which is a continuation of application No. 07/908,895, filed on Jul. 8, 1992, now abandoned, which is a continuation of application No. 07/664,503, filed on Mar. 5, 1991, now abandoned, which is a continuation of application No. 07/518,302, filed on May 2, 1990, now abandoned, which is a continuation of application No. 07/128,341, filed on Nov. 20, 1987, now abandoned.

(30) Foreign Application Priority Data

Mar. 21, 1986 (GB) ............................................ 86400609

(51) Int. Cl.[7] ............................ C12Q 1/70; C12Q 19/34
(52) U.S. Cl. .................... 435/5; 435/91.1; 435/91.33; 424/204.1; 536/23.72; 536/23.1; 930/220
(58) Field of Search ...................... 435/5, 91.1, 91.33; 536/23.72, 23.1; 930/220; 424/204.1

(56) References Cited

U.S. PATENT DOCUMENTS

| | | | |
|---|---|---|---|
| 4,358,535 A | 11/1982 | Falkow et al. | |
| 4,419,446 A | 12/1983 | Howley et al. | |
| 4,551,270 A | 11/1985 | Danos et al. | |
| 4,748,109 A | 5/1988 | Baird | |
| 4,849,331 A | 7/1989 | Lorincz | |
| 4,849,332 A | 7/1989 | Lorincz | |
| 4,849,334 A | 7/1989 | Lorincz | |
| 4,983,728 A | 1/1991 | Herzog et al. | |
| 5,057,411 A | 10/1991 | Lancaster et al. | |
| 5,411,857 A | 5/1995 | Beaudenon et al. | |
| 5,554,538 A | 9/1996 | Cole et al. | |

FOREIGN PATENT DOCUMENTS

| | | |
|---|---|---|
| EP | 0 192 001 A2 | 8/1986 |
| EP | 0 425 955 A2 | 5/1991 |
| EP | 0 477 972 A2 | 4/1992 |
| EP | 0 489 442 A1 | 6/1992 |
| WO | 90/02821 | 3/1990 |
| WO | 91/08312 | 6/1991 |
| WO | 91/19812 | 12/1991 |

OTHER PUBLICATIONS

Orth, et al., "Papillom avirus . . . infections" *Chem. Abst.* 106(25):348, abst. 210547s, issued Jun. 22, 1987.
Rev. Pfister, *Biochem. Pharm*, 99:111–181 (1983).
Rando, et al. *J. Virol.* 57:353–356 (1986).
Riov, et al. *C.R. Acad. Sci*, Ser III 14:575–580 (1984).
Suggs, et al. *Proc Nat'l Acad. Sci.* 78:6613–6617 (1981) Associated with Epiderm odysplasia Verruciformis *J. Virol.* 43(2):436–447 (1982).
Chen et al. "The primary structure and genetic organization of the bovine papillom avirus type 1 genome" *Nature* 299:529–534 (1982).
Danos, et al. *EMBO* 1(2):231–236 (1982).
Howley "The Human Papillom aviruses" *Arch Pathol. Lab. Med.* 106:429–432 (1982).
M. Kawashima, et al. "Characterization of a New Type of Human Papillomavirus Found in a Lesion of Bowen's Disease of the Skin," *J. Virol* 57(2):688–682 (Feb. 1986).
K. Seedorf, et al. "Human Papillomavirus Type 16 DNA Sequence," *Virol.* 145:181–85 (1985).
D. Kremsdorf, et al. "Molecular Cloning and Characterization of Genomes of Nine Newly Recognized Human Papillom avirus Types Associated with Epiderm odysplasia Verruciformis," *J. Viol.* 52(3):1013–18 (Dec. 1984).
R. Barrasso, et al. "Lésions Génitales Masculines a Papillom avirus. Intérét de la Colposcopie," Ann. Dermator. Venereol. 113:787–795 (F rance 1986).
S. Beaudenon, et al. "A Nov el type of human Papillom avirus associated with genital neoplasias," *Nature* 321:246–249 (1986).

(List continued on next page.)

*Primary Examiner*—Ali R. Salimi
(74) *Attorney, Agent, or Firm*—Finnegan, Henderson, Farabow, Garrett & Dunner, L.L.P.

(57) ABSTRACT

The invention concerns DNA fragments derived from the genomic DNA of HPV-33. These fragments are selected from the group of fragments extending between the nucleotide extremities defined hereafter in relation to the nucleotide-numbering in FIGS. 1a and 1b respectively:

76–556
543–864
867–2811
2728–3808
3326–3575
3842–4079
4198–5611
5516–8091

The invention also relates to the use of these fragments as probes for the detection of HPV in tissue cultures.

30 Claims, 3 Drawing Sheets

OTHER PUBLICATIONS

J.R. Coggin, Jr., et al. Meeting Report, Workshop on Papillim avirus and Cancer, Cancer Res. 39:545–546 (1979).

B. Parent, et al. "Les dy splasies du col utérin," *J. Gynecol Obstet. Biol. Reprod.* 15:941–947 (1986).

P.H. Pouwels, et al. Cloning Vectors, A Laboratory Manual, VIII:1–3, 5–7 (Elsev ier, Amsterdam 1985).

E. Schwarz, et al. "DNA sequence and genom e organization of genital human papillom avirus type 6b," *EMBO J.* 2(12):2341–2348 (1983).

K. Seedorf, et al. "Human Papillom avirus Type 16 DNA: Expression of Open Reading F rames in *E. coli*" ULCA Symp. Mol. Cell. Biol., New Ser. vol. 32: Papillom aviruses: Molecular and Clinical Aspects:391–396 (Alan R. Liss, Inc. 1985).

D. Kremsdorf, et al. "Biochemical Characterization of Two Types Human Papillom aviruses Associated with Epiderm odysplasia Verruciformis" *J. Viol.* 43(2):436–447 (1982).

D. Kremsdorf, et al. "Human Papillom aviruses Associated with Epiderm odysplasia Verruciformis. II. Molecular Cloning and Biochem ical Characterization of Human Papillom avirus 3a, 8, 10, and 12 Genomes," *J. Virol.* 48(2):340–351 (1983).

S.T. Cole, et al. "Genome Organization and Nucleotide Sequence of Human Papillom avirus Type 33, Which is Associated with Cerv ical Cancer" *J. Virol.* 58(3):991–995 (1986).

S.T. Cole, et al. "Nucleotide Sequence and Com parative Analysis of the Human Papillom avirus Type 18 Genome: Phylogeny of Papillom aviruses and Repeated Structure of the E6 and E7 G ene Products" *J. Mol. Biol.* 193(4):599–608 (1987).

M. Durst, et al. "A papillom avirus DNA from a cervical carcinoma and its prevalence in cancer biopsy samples from different geographic regions" *Proc. Natl. Academ y Sci. USA* 80:3812–3815 (1983).

L. Gissmann, et al. "Hum an papillom avirus types 6 and 11 DNA sequences in genital and lary ngeal papillom as and in some cervical cancers" *Proc. Natl. Academ y Sci. USA* 80:560–563 (1983).

Katina et al., *EMBO* 1(2):231–236 (1982).

Lancaster, et al. "Hum an Papillom avirus . . . Uterine Cervix" *Chem Abst.* 99(3):218, abst. 188882k, issued Dec. 5, 1983.

```
7500                          Z                              78-1
TAACCGTTTTCGGTTACTTGGCATACATACCCTATGACATTGGCAGAACAGTTAATCCTT
                                              Z              78-2
TTCTTTCCTGCACTGTGTTTGTCTGTACTTGCTGCATTGGCATACATACCCTATGACATT

GGCAGAACAGTTAATCCTTTTCTTTCCTGCACTGTGTTTGTCTGTACTTGCTGCATTGAC

TCATATATACATGCAGTGCAATTGCAAAATACTTAATTGTACTAATAGTTTACACATCCT

TTTAGGCACATATTTTTACTTTACTTTCAAACCTTAAGTGCAGTTTTGGCTTACACAATT

GCTTTGTATGCCAAACTATGCCTTGTAAAAGTGAGTCACTACCTGTTTATTACCAGGTGT

GGACTAACCGTTTTAGGTCATATTGGTCATTTATAATCTTTTATATAATAGTAAACTATA

ATGCCAAGTTTTAAAAAAGTAGGGTGTAACCGAAAGCGGTTCAACCGAAAACGGTGCATA

TATAAAGCAAACATTTTGCAGTAAGGTACTGCACGACTATGTTT
                                E6......MetPhe
```

FIG.3

DETERMINED DNA SEQUENCED DERIVED FROM A PAPILLOMAVIRUS GENOME, THEIR USES FOR IN VITRO DIAGNOSTIC PURPOSES AND THE PRODUCTION OF ANTIGENIC COMPOSITIONS

This is a continuation of application Ser. No. 09/577,493, filed May 25, 2000, now U.S. Pat. No. 6,242,250; which is a continuation of Ser. No. 09/330,076, filed Jun. 11, 1999, issued as U.S. Pat. No. 6,107,086, Ser. No. 08/789,781, filed Jan. 28, 1997, abandoned; which is a continuation of Ser. No. 08/466,711 filed Jun. 6, 1995 issued as U.S. Pat. No. 5,648,459; which is a divisional of Ser. No. 08/222,569 filed Mar. 25, 1994, issued as U.S. Pat. No. 5,554,538; which is a continuation of Ser. No. 08/161,239 filed Nov. 10, 1993, abandoned; which is a continuation of Ser. No. 08/032,694 filed Mar. 17, 1993, abandoned; which is a continuation of Ser. No. 07/908,895 filed Jul. 8, 1992, abandoned; which is a continuation of Ser. No. 07/664,503 filed Mar. 5, 1991, abandoned; which is a continuation of Ser. No. 07/518,302 filed May 2, 1990, abandoned; which is a continuation of Ser. No. 07/128,341 filed Nov. 20, 1987, abandoned; all of which are incorporated herein by reference.

The invention pertains to determined DNA sequences derived from a papillomavirus genome, more particularly DNA recombinants, including vectors, modified by such DNA sequences in such manner that, when said DNA recombinants are introduced in suitable host cells in which said DNA recombinants can be replicated, the said DNA sequences can be expressed in the form of the corresponding proteins. The invention further relates to the proteins themselves, which can be purified and used for the production of immunogenic compositions.

The invention pertains more particularly to DNA products of the papillomavirus designated as IP-2 (now redesignated as HPV-33) in the European patent application filed under number 85.402362.9 on Nov. 29, 1985, the contents of which are incorporated herein by reference. A plasmid containing the DNA of said virus has been deposited at the CNCM ("Collection nationale de Culture de Micro-Organismes" of the Pasteur Institute of Paris) under number I-450.

Papillomaviruses are members of the papovavirus family and possess a genome of about 7,900 base pairs (bp) consisting of a covalently closed circular DNA molecule. Human papilloma viruses (HPV) are classified on the basis of their DNA sequence homology (6) and nearly 40 types have now been described. Considerable insight into HPV biology and their involvement in human disease has been attained by the application of the techniques of molecular biology. A possible role for HPVs in human cancer was suspected following the detection of HPV DNA in tumors resulting from the malignant conversion of genital warts (33). The cloning of two HPV genomes, HPV-16 and HPV-18 (3, 11) from cervical carcinomas has further stimulated research in this field of immense socio-economic importance. These viruses were discovered in more than 70% of the malignant genital tumors examined and in many others HPV-16 related sequences were detected (3, 16, 33). Amongst these is HPV-33 which was recently cloned from an invasive cervical carcinoma using HPV-16 as a probe under conditions of reduced stringency (1). In the present study we have determined the DNA sequence of HPV-33 and describe its relationship to HPV-16. Among the papillomaviruses HPV-33 is unique as it possesses a 78 bp tandem repeat which strongly resembles the enhancer of SV40 (4, 14).

The invention stems from the cloning strategy disclosed hereafter of the genome of HPV-33 which enabled particular DNA sequences to be identified, more particularly those providing hybridization probes, particularly useful for the detection of DNA of papillomaviruses related to HPV-33 in human tissue, whereby positive responses can be related to the possible development in the host of invasive cervical carcinomas.

Reference is hereafter made to the drawings in which the figs concern respectively.

Preferred sequences are those which encode full proteins, more particularly and respectively the nucleotidic sequences having the open reading frames referred to in table I hereafter.

The conditions under which the DNA sequence analysis were performed are defined under the heading "MATERIALS AND METHODS" hereafter. The conclusions which were drawn from this sequence analysis appear under the heading "DISCUSSION".

MATERIALS AND METHODS

DNA sequence analysis, The source of HPV-33 sequenced in this study was plasmid p15-5 (1) which consists of a BglII linearized HPV-33 genome cloned in a pBR322 derivative. A library of random DNA fragments (400–300 bp) was prepared in M13mp8 (17) after sonication and end-repair of p15-5, essentially as described previously (28). DNA sequencing was performed by the dideoxy chain termination method (19, 20) with the modifications of Biggin et al. (2). Most of the seQuence was derived in this way although part of the non-coding region was found to be absent or under-represented in the M13 library (>300 clones). The sequence of this region was obtained directly from p15-5 using the method of Smith (24). Briefly, restriction fragments isolated from 2 "complemenary" M13 clones were used to prime DNA synthesis on templates prepared from p15-5 which had been linearized with a restriction enzyme and then treated with exonuclease III (200 units/pmol DNA for 1 h at 22° C.). Computer analysis, DNA sequences were compiled and analysed with the programs of Staden (26, 27) as modified by B. Caudron. Optimal alignments of DNA or protein sequences were obtained using the algorithm developed by Wilbur and Lipman (31).

RESULTS AND DISCUSSION

Figure 1A:
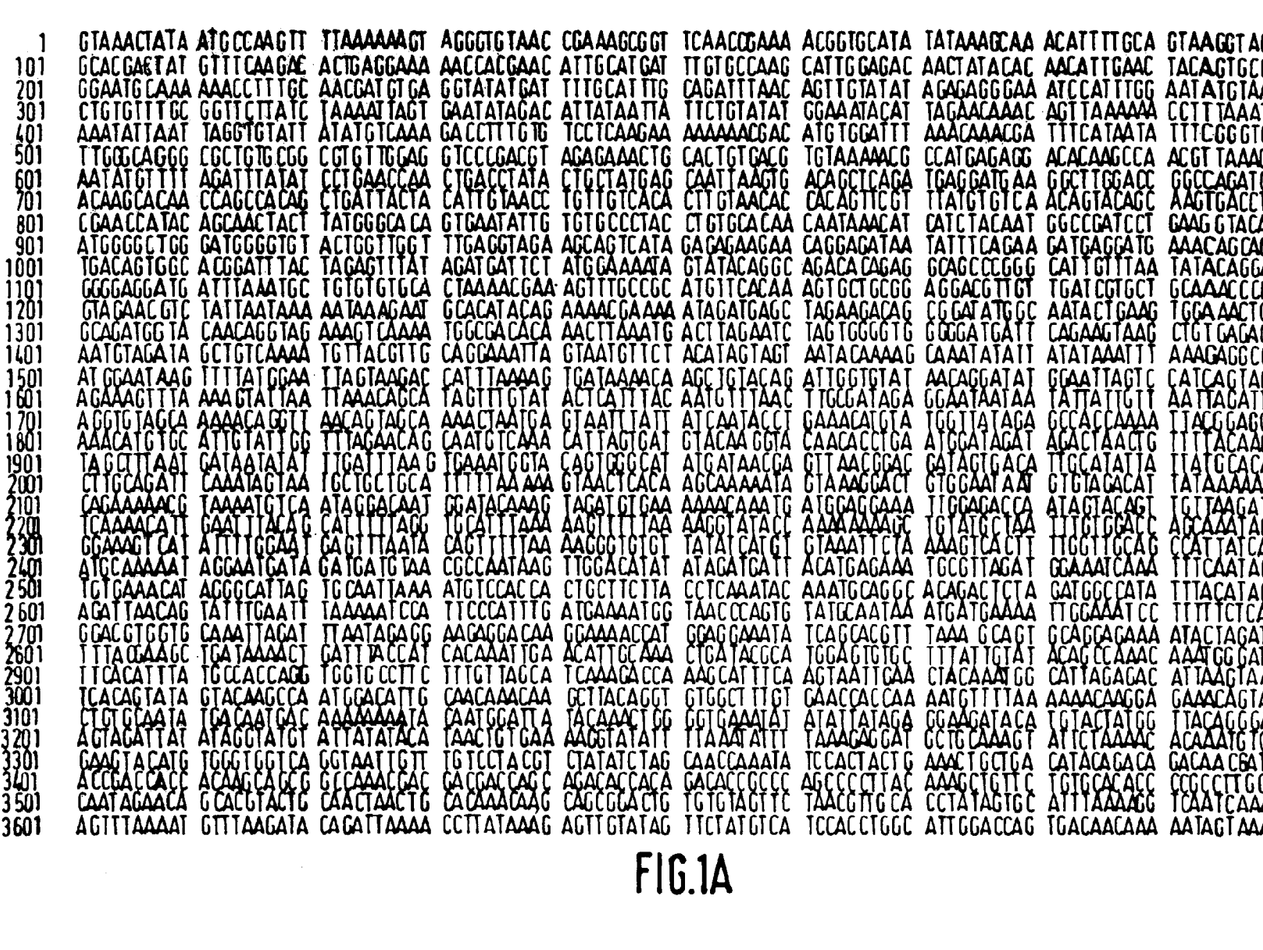
FIGS. 1a and 1b. Nucleotide sequence of HPV-33. Position 1 on the circular genome corresponds to a "Hpa-like" sequence found by alignment with HPV-6b.
Figure 1B:
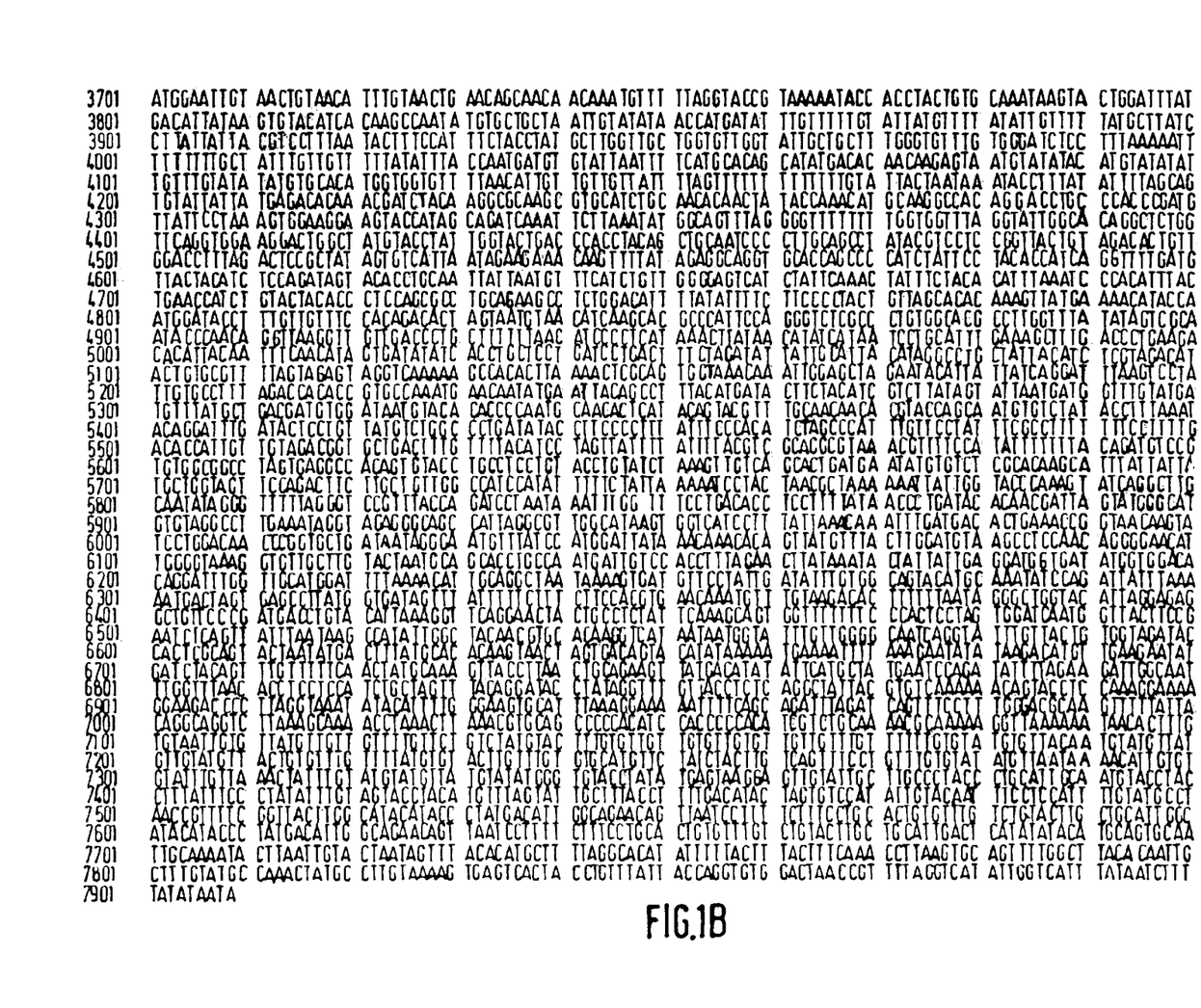

Genomic Arrangement of HPV-33—The complete 7909 nucleotide sequence of HPV-33, determined by the M13 shotgun cloning/dideoxy sequencing approach, is presented in FIG. 1. On average each position was sequenced 6.5 times. In agreement with the convention for other papillomavirus sequences the numbering begins at a site resembling the recognition sequence for HpaI in the non-coding region.

Figure 2:
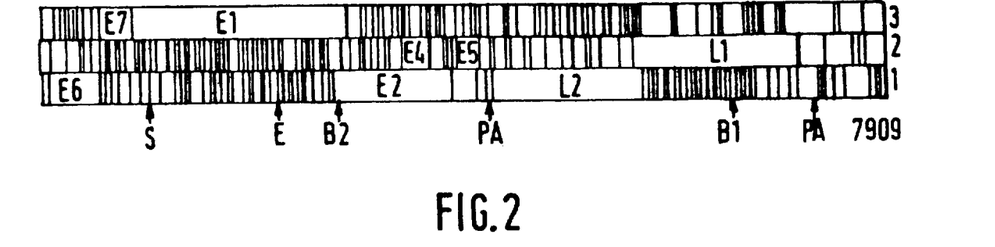
FIG. 2. Distribution of the major reading frames in the HPV-33 genome the reading frames were identified by comparison with other HPV sequences and the stop codons are represdented as vertical bars. Also indicated are the locations of unique restriction sites (S, SmaI; E, EcoRV; B2, BglII; B1, BglI) and the likely polyadenylation signals (PA) for the early and late transcripts. In addition to these, 6 other potential PA sites (AATAAA) were detected at positions 662, 1215, 1221, 2666, 5837 and 6239.

An analysis of the distribution of nonsense codons (FIG. 2) shows that, as in all other sequenced papillomaviruses, the 8 major open reading frames are located on the same strand. Some features common to HPV-33 and HPV types 1a, 6b and 16 together with the cottontail rabbit papillomavirus and the prototype bovine papillomavirus, BPV-1, (5, 7, 8, 13, 21, 22) include the overlap between the largest open reading frames in the early region, E1 and E2, and the inclusion of E4 within the section encoding E2. Interestingly, the BglII site used in the molecular cloning of HPV-33 is situated within the E1/E2 overlap. Another property common to all papillomaviruses, except BPV-1, is the overlap between the L1 and L2 reading frames. Following L1 is the 892 bp non-coding region which, by analogy with BPV1 (15, 29) undoubtedly contains the origin of replication and various transcriptional regulatory elements. The principal characteristics of the HPV-33 genome are summarized in Table 1.

Nucleotide Sequence Comparison with HPV-16—HPV-16 is the only other oncogenic papillomavirus, isolated from tumors of the ano-genital region, which has been completely sequenced (22). The gross features of HPV-33 resemble those of HPV-16 except that the El reading frame of the latter is interrupted. All of the coding sequences in HPV-33, except that of E5, are slightly shorter than their counterparts in HPV-16. This may contribute to the fact that its non-coding region, between L1 and E6 (FIG. 2), is 76 bp longer thereby keeping the genomes nearly constant in size.

When the open reading frames were compared pairwise (Table 2) it was found that E1, E2, E6, E7, L1 and L2 displayed between 65–75% homology whereas those for E4 and E5 were more divergent (about 50% homology). These findings confirm the heteroduplex analysis performed previously (1). A comparative study (8) of papillomavirus E1 gene products showed that the polypetide consists of an NH$_2$-terminal segment whose sequence is highly variable, and a COOH-terminal domain of well-conserved primary structure. The longest stretch of perfect sequence homology, 33 nucleotides (positions 1275–1307, FIG. 1) is found near the 5'-end of the E1 reading frame in a region encoding the variable domain of the polypeptide. Several other regions of complete identity (19–28 nucleotides) were detected elsewhere in E1, and also in E2, L2 and L1. As many of these sequences are not found in the genomes of other HPVs, such as HPV-1a and HPV-6b, this raises the possibility that the corresponding oligonucleotides could be produced and used as diagnostic hybridization probes for screening biopsy material from potentially tumorigenic lesions.

Potential Gene Products—The papillomavirus gene products may be divided into those which are believed to play a purely structural role, L1 and L2, and those required for viral propagation and persistence. The results of a comparison of the probable products of the major reading frames from HPVs-33, 16 and 61b are summarized in Table 2. As expected there is strong identity between the ocogenic HPVs-33 and 16, particularly for the proposed E1, E6, E7, L2 and L1 proteins. When conservative substitutions are included the homology between the two L1 polypeptides increases to 90% suggesting that the corresponding capsids must be antigenically related. In contrast, significantly weaker homologies were detected when the analysis was extended to include the benign genital wart-forming HPV-6b (Table 2). Comparison of the HPV-16 proteins with those of HPV-6b revealed slightly more homology than was found with HPV-33 suggesting a closer evolutionary relationship.

The non-coding Region—The non-coding region of HPV-33 displays several unique properties and bears only weak resemblance to its homologue in HPV-16. Located between the L1 stop codon and including the putative polyadenylation signal for the late transcripts is a stretch of 223 bp (positions 7097–7320, FIG. 1) unusually rich in T+G (79%). Contained within this segment are two copies of a 19 bp direct repeat (with one mismatch) and 7 copies of the motif TTGTRTR (where R is A or G). The latter is also found 7 times in the corresponding region of HPV-16 suggesting that it may represent a recognition site for proteins involved in replication. It should be noted that nascent replication forks have been localised in this regiion of the BPV-1 genome (29) and that the origin of replication of the Epstein-Barr virus consists of a family of repeated sequences (32).

A 12 bp palindrome (ACCG . . . CGGT) that occurs exclusively in the non-coding region of all papillomavirus genomes examined was recently reported by Dartmann et al. (9). Three copies were found in the HPV-33 genome (FIG. 3) and these occupy the same positions in the non-coding region of HPV-16. A role for the palindrome as a possible control site for the early promoter was proposed (4, 9, 35 15) and indirect support is provided by our finding that the non-coding regions of HPVs, such as HPV-33, do not display the clustered arrangement of recognition sites for the promoter-specific, activation factor Sp1 (12). This is in direct contrast to the situation in another papovavirus, SV40 (12, 14).

Figure 3:
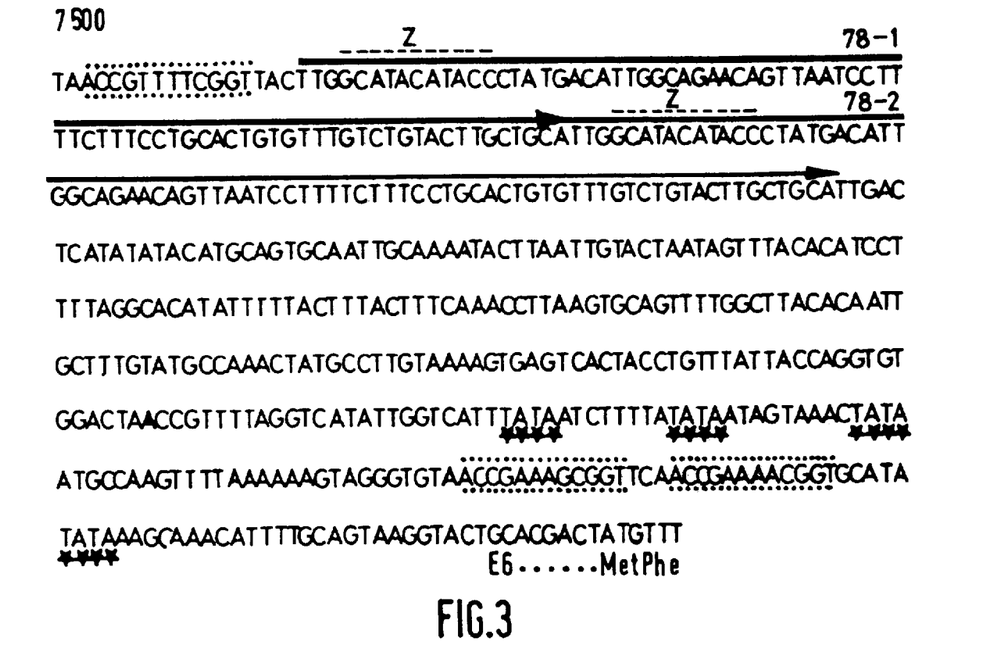
FIG. 3. Principle features of the non-coding region. A section of the non-coding region from positions 7500 to 114 is shown. The 78 bp tandem repeats are overlined and those regions resembling the Z-DNA forming element of the SV-40 enhancer are indicated. Potential promoter elements are denoted by stars and the 3 copies of the 12 bp palindrome enclosed between two rows of dots.

The most striking feature of HPV-33 is a perfect 78 bp tandem repeat located 200 bp after the putative origin of replication (FIG. 3). No other repeats of this size or sequence have been described in the genomes of other papillomaviruses. The presumed early promoter for HPV-33 is located about 300 bp downstream from the tandem repeat and the characteristic promoter elements (4) could be identified (FIG. 3). The size, position and arrangement of the 78 bp repeats in the HPV-33 genome suggest that they may function as enhancers of viral transcription. Tandem repeats of 72, 73 and 68 bp have been located near the early promoter of SV40 (4, 14), in the LTR of moloney murine sarcoma virus (10), and in the BK virus genome (23) and shown to enhance transcription from PolII dependent promoters in a cis-active manner. From mutagenesis of the SV40 enhancer (14, 30) and sequence comparisons of characterized transcriptional activators a consensus enhancer sequence was derived. This structure could not be detected in the 78 bp repeat but a potential Z-DNA forming region was uncovered. Z-DNA is believed to attract regulatory molecules to eukaryotic promoters and a Z-DNA antibody binding site has been demonstrated within the SV40 enhancer (18). The sequence to which this antibody binds is also found, albeit with a single mismatch, in the putative HPV-33 enhancer (positions 7520–7527, 7599–7606, FIGS. 1, 3).

The proposed HPV-33 enhancer shows no extended sequence homology to the well-characterized enhancers nor to other papillomavirus regulatory regions. However, it has recently been demonstrated that an enhancer-like element is located in the non-coding region of BPV-1 and that it requires the E2 product for activation (25). These findings support our proposal that the 78 bp tandem repeats could have enhancer function and may indicate that the relatively low homology (Table 2) between the E2 proteins of HPV-33 and 16 reflects a specificity for the corresponding enhancer/regulatory regions.

Tables 1 and 2 which have been referred to in the instant disclosure follow.

TABLE 1

Principal features of the HPV-33 genome

| Open Reading Frame | START | FIRST ATG | STOP CODON | mol. wt. |
|---|---|---|---|---|
| E6 | 76 | 109 | 556 TGA | 17 632 |
| E7 | 543 | 573 | 654 TAA | 10 825 |
| E1 | 867 | 879 | 2811 TGA | 72 387 |
| E2 | 2728 | 2749 | 3808 TAA | 40 207 |
| E4 | 3326 | — | 3575 TAG | 9 452 |
| E5 | 3842 | — | 4079 TAA | 9 385 |
| L2 | 4198 | 4210 | 5611 TAG | 50 539 |
| L1 | 5516 | 5594 | 7091 TAA | 55 839 | a. Calculated from the first ATG where this exists or from the start of the open reading frame.

TABLE 2

Comparison of HPV proteins[a]

| | HPVs | HPVs | |
|---|---|---|---|
| Protein | 33v16 | 33v6b | 16v6b |
| E6 | 65(70) | 36(51) | 37 |
| E7 | 61(69) | 55(60) | 56 |
| E1 | 61(69) | 50(60) | 53 |
| E2 | 53(65) | 46(58) | 45 |
| E4 | 52(55) | 39(46) | 48 |
| E5 | 40(52) | 39(43) | 33 |
| L2 | 64(66) | 52(58) | 53 |
| L1 | 81(75) | 68(69) | 71 |

[a]-Expressed as % homology after alignment with the program of (31). Values in parenthesis represent % nucleotide sequence homology.

The invention relates more particularly to sequences corresponding to the open reading frames of E6, E7, E1, E2, E4, E5, L2, L1.

The invention pertains also the uses of these sequences as hybridization probes, either those which are useful also for the detection of other papillomaviruses, thus of groups of papillomaviruses—such as probes containing part or all of the open reading frames corresponding to L1—or those which are more virus—specific, i. e. probes containing part or all of the open reading frame corresponding to.

It also relates to other probes which detect sub-groups of papillomaviruses, particularly probes for the detection of viruses which can be related to major classes of diseases, i. e. viruses associated with tumors. By way of example of one of said probes one should mention that which contains the sequence positionned between nucleotides 1275 and 1307 according to the numbering of the nucleotides in FIGS. 1A, 1B.

Needless to say that the invention also pertains to all of said DNA sequences, when labelled by a suitable label, i. e. a radioactive enzymatic or immunofluorescent label.

DNAs derived from the viral genome and which carry nucleotides modified by a chemical group which can be recognized by antibodies also form part of the invention. It is well known that such DNAs can be produced by nick-translation in the presence of nucleotides modified accordingly. These DNAs form particularly valuables hybridization probes which, when hybridized to a DNA preparation containing the complementary strand sought, can be detected by the above mentioned antibodies.

The invention also pertains to the diagnostic methods per se. Suitable methods are exemplified hereafter.

Several hybridization methods may be used. For example, the spot hybridization method includes, after denaturation of the DNA, the deposition of an aliquot of the DNA onto film supports (nitrocellulose or Genescreenplus), the hybridization of each film under the usual conditions with the probe, and the detection of the radioactive hybrid by contact exposition of the hybridized film onto radiographic film. Another possibility is replicated culture hybridization which involves agarose gel electrophoresis separation of the DNA fragments resulting from treatment of the DNA by restriction enzymes, the transfer of the fragments after alkaline denaturation onto films (nitrocellulose or Genescreenplus) and their hybridization under usual conditions with different mixtures of probes. The formation of radioactive hybrids is detected again by contact exposition of the hybridization support films onto radiographic film.

For instance the probes of the invention can be used for the detection of the relevant viruses (or DNAs thereof) in preparation consisting of a biopsy of cells obtained by scraping a lesion, or of biopsy sections fixed with Carnoy's mixture (ethanol, chloroform, acetic acid 6:3:1) and included in paraffin.

The above nucleotide sequences can be inserted in vectors, to provide modified vectors which, when introduced in the suitable cell host, are capable of providing for the transcription and, where appropriate, translation of said DNA sequences to produce the corresponding proteins which can then be isolated from cellular extracts of the hosts. Obviously it is within the knowledge of the man skilled in the art to select the appropriate vectors, particularly in relation to the host to be transformed therewith. Vectors consist for instance of plasmids or phages which will be selected according to their recognized capability of replicating in the corresponding procaryotic cells (or yeast cells) and of allowing for the expression of the DNA sequence which they carry.

The invention also relates to DNA recombinants containing an insert consisting of a DNA sequence corresponding to any of the above-defined open reading frames or of a part thereof, and suitably engineered to allow for the expression of the insert in eucaryotic cells, particularly cells of warm-blooded animal. Suitable DNA recombinants are genetic constructs in which said insert has been placed under the control of a viral or eucaryotic promoter recognized by the polymerases of the selected cells and which further comprise suitable polyadenylation sites downstream of said insert.

By way of example, the invention pertains to DNA recombinants containing any of the above-mentioned open-reading inserts placed under the control of a promoter derived from the genome of the SV40 virus. Such DNA recombinants—or vectors—can be used for the transformation of higher eucaryotic cells, particularly cells of mammals (for instance Vero cells). The invention further pertains to portions of the above identified DNA sequences which, when inserted in similar vectors, are able to code for portions of the corresponding proteins which have immunological properties similar to those encoded by the full nucleotide sequences mentioned above. The similarity of immunological properties can be recognized by the capacity of the corresponding polypeptides produced by the relevant host to be recognized by antibodies previously formed against the proteins produced by the cells previously transformed with vectors containing the above mentioned entire DNA sequences.

It goes without saying that the invention also pertains to any nucleotidic sequence related to the preceding ones which may be obtained at least in part synthetically, and in which the nucleotides may vary within the constrainsts of the genetic code, to the extent where these variations do not entail a substantial modification of the polypeptidic sequences encoded by the so-modified nucleotidic sequences.

It already flows from the preceding discussion that the invention also pertains to the purified proteins or polypeptides themselves as obtainable by the methods discussed hereabove. These polypeptides, when produced in a suitable host, can either be obtained from the cells, for instance after rupturing of their cell walls, or from the culture medium of said cells when excreted in said cell medium, depending on the cell DNA recombinant system which is used. The polypeptide obtained can then be purified by resorting to usual purification procedures. It should be understood that "purified" in the instant context means a level of purity such that, when electrophoresed in SDS-PAGE, the purified proteins yield a single detectable band, say by western blot.

The viral proteins obtained, more particularly the structural proteins, for instance as a result of the expression of said DNA sequences in E. coli, can be used for the in vitro detection of antibodies against papillomavirus likely to be detected in tissue samples of patients possibly infected with papillomavirus.

Of particular relevance are the genetically engineered proteins having the peptidic sequences which can be deduced from the L1 and L2 open reading frames. Another peptide of interest is the E6 * protein (E6 star), the synthesis of which can be induced by splicing and which encoded by a nucleotidic sequence located between nucleotides 229 (donor site) and 404 (acceptor site) of the HPV 33 sequence (see more particularly FIG. 1A), which sites also define the putative splicing sites in the E6 * open reading frame of HPV 33. Reference may be had to the publication of Schneider-Gardicke and Schwartz, Embo. J. , 5, 2285–2292, as concerns the conditions of the production of such proteins.

These purified polypeptides can in turn be used for the production of corresponding antibodies which can be used for diagnosing in vitro the presence of viral polypeptides in a biological fluid, particularly in a serum or tissue culture of a patient. Like in the preceding instance, the invention relates to portions of the above defined polypeptides, particularly those which are recognized by the same antibodies or to the contrary are able to elicit in vivo the production of antibodies recognizing the complete proteins.

It must be understood that the inventions relates also specifically to the particular peptides encoded by the DNA regions specifically referred to in the preceding disclosure and which have been found of particular interest.

The invention further concerns host cells transformed with DNA recombinants containing nucleotidic sequences directing the expression of the different peptides mentioned hereabove, and effectively capable to produce said peptides when cultured in an appropriate culture medium.

The invention finally also pertains more particularly to the antibodies themselves which can be obtained from an animal, such as rabbit, immunized in standard manner with said purified polypeptides and/or from hybridomas previously prepared also in any known manner. Of particular inerest are the antibodies (polyclonal and monoclonal antibodies) directed against the strutural proteins. These antibodies are useful for the detection of viral infection. The antibodies which recognize the L1, L2 and E6 * proteins of HPV-33 are of particular significance. Antibodies specific of L2 provide diagnostic tools for the in vitro detection of specific viruses sharing with HPV-33 a sequence encoding a similar L2 protein. Antibodies specific to L1 are useful for the detection of the groups of viruses, to which HPV-33 belongs. Antibodies specific to the E6 * protein are useful for the detection of the oncogenic character of the virus causing the abovesaid viral infection.

The invention also relates to intergenic sequences of particular interest, particular the 78 bp sequence. This sequence is of particular interest as a possible insert in eucaryotic vectors, particularly in a position upstream of the promoter and downstream of the site at which transcription of the gene or nucleotide sequence the transcription of which is sought is initiated in the relevant host.

All documents referred to herein are incorporated herein by reference. Particularly these documents can be referred to as concerns the definition of expressions used in this application where appropriate. As such they form part of the present disclosure.

BIBLIOGRAPHY

1. Beaudenon, S.
2. Biggin, M. D., T. J. Gibson, and G. F. Hong. 1983 Buffer gradient gels and $^{35}$S label as an aid to rapid DNA sequence determination. Proc. Natl. Acad. Sci. USA. 80, 3963–3965.
3. Boshart, M. , L. Gissmann, H. Ikenburg, A. Kleinheinz, W. Scheurlen, and H. Zur Hausen. 1984. A new type of papilloma-virus DNA, its presence in genital cancer biopsies and in cell lines derived from cervical cancer. EMBO J. 3, 1151–1157.
4. Breathnach, R. and P. Chambon. 1981. Organization and expression of eukaryotic split genes coding for proteins. Ann. Rev. Biochem. 50, 349–383.
5. Chen, Y. , P. M. Howley, A. D. Levinson and P. M. Seeburg. 1982. The primary structure and organization of the bovine papillomavirus (BPV) type 1 genome. Nature 299, 529–534.
6. Coggin, J. R. and H. Zur Hausen. 1979. Workshop on papillomaviruses and cancer. Cancer Res. 39, 545–546.
7. Danos, O. , M. Katinka, and M. Yaniv. 1982. Human papillomavirus la DNA sequence: a novel type of genome organization among papovaviridae. EMBO J. 1, 231–236.
8. Danos, O. , I. Giri, F. Thierry and M. Yaniv. 1984. Papillomavirus genomes: sequences and consequences. J. Investig. Dermatol. 83, 75–115.
9. Dartmann, K. , E. Schwarz, L. Gissmann and H. Zur Hausen. 1985. The nucleotide sequence and genome organization of human papillomavirus type 11. Virology. In press.
10. Dhar, R. , W. L. McClements, L. W. Enquist and G. F. Vande-Woude, 1980. Nucleotide sequence of integrated Moloney sarcoma provirus long terminal repeats and their host and viral functions. Proc. Natl. Acad. Sci. USA 77, 3937–3941.
11. Durst, M. , L. Gissmann, H. Ikenburg and H. Zur Hausen 1983. A new type of papillomavirus DNA from a cervical carcinoma and its prevalence in genital cancer biopsies from different geographic regions. Proc. Natl. Acad. Sci. USA. 80, 3812–3815.
12. Dynan, W. S. and R. Tijan. 1985. Control of eukaryotic messenger RNA synthesis by sequence-specific DNA-binding proteins. Nature 316, 774–778.
13. Giri, I. , O. Danos and M. Yaniv. 1985. Genomic structure of the cottontail rabbit (Shope) papillomavirus. Proc. Natl. Acad. Sci. USA. 82, 1580–1584.
14. Gruss, P. , R. Dhar and G. Khoury. 1981 Simian virus 40 tandem repeated sequences as an element of the early promoter. Proc. Natl. Acad. Sci. USA 78, 943–947.
15. Howley, P. M. , Y. C. Yang and M. S. Rabson. 1985. The molecular biology of bovine papillomaviruses. pp. 67–81 in P. W. J. Rigby and N. M. Wilkie (eds). "Viruses and Cancer", Society for General Microbiology Symposium, 37, Cambridge University Press, Cambridge.
16. Ikenburg, H. , L. Gissmann, G. Gross, E. I. GrussendorfConen and H. Zur Hausen. 1984 Human Papillomavirus type-16 related DNA in genital Bowen's disease and in Bowenoid papulosis. International Journal of Cancer 32, 563–565.
17. Messing, J. and J. Vieira. 1982: A new pair of M13 vectors for selecting either DNA strand of double digest restriction fragments. Gene 19, 269–276.
18. Nordheim, A. and A. Rich. 1983. Z-DNA Formation in the enhancer region of supercoiled SV40. pp. 45–50. in Enhancers and Eukaryotic Gene Expression, Cold Spring Harbor Laboratory, Cold Spring Harbor, N. Y.
19. Sanger, F. , S. Nicken, A. R. Coulson. 1977. DNA sequencing with chain terminating inhibitors, Proc. Natl. Acad. Sci. USA 74, 5463–5467.
20. Sanger, F. , A. R. Coulson, B. G. Barrel, A. J. H. Smith, B. A. Roe, 1980. Cloning in single stranded bacteriophage as an aid to rapid DNA sequencing. J. Mol. Biol. 143, 161–178.
21. Schwartz, E. , M. Dürst, C. Demenkowski, O. Lattermann, R. Zech, E. Wolfsperger, S. Suhai and H. Zur Hausen, 1983. DNA sequence and genome organization of genital human papillomavirus type 6b. EMBO J. 2, 2361–2368.
22. Seedorf, R. , G. Krammer, M. Dürst, S. Suhai and W. G. Rowenkamp, 1985. Human papillomavirus type 16 DNA sequence. Virology 145, 181–185.
23. Seif, I. , G. Khoury and R. Dhar. 1979. The genome of human papovavirus BKV. Cell 18, 963–977.
24. Smith, A. J. H. 1979. The use of exonuclease III for preparing single stranded DNA for use as a template in the chain terminator sequencing method. Nucleic Acids Res. 6, 831–848.
25. Spalholz, B. A. , Y. C. Yang and P. M. Howley. 1985. Transactivation of a bovine papillomavirus transcriptional regulatory element by the E2 gene product. Cell 42, 183–191.
26. Staden, R. 1979. A strategy of DNA sequencing employing computer programs. Nucleic Acids Res. 6, 2601–2610.
27. Staden R. 1980. A new computer method for the storage and manipulation of DNA gel reading data. Nucleic Acids Res. 8, 3673–3694.
28. Wain-Hobson, S. , P. Sonigo, O. Danos, S. Cole, and M. Alizon. 1985. Nucleotide sequence of the AIDS virus, LAV. Cell 40, 9–17.
29. Waldeck, W. , F. Rosl, and H. Zentgraf. 1964. Origin of replication in episomal bovine papilloma virus type 1 DNA isolated from transformed cells. EMBO J. 3, 2173–2178.
30. Weiher, H. , M. Konig, and P. Gruss. 1983. Multiple point mutations affecting the simian virus 40 enhancer. Science 219, 626–631.
31. Wilbur, W. J. and D. J. Lipman. 1983. Rapid similarity searches of nucleic acid and protein data banks. Proc. Natl. Acad. Sci. USA 80, 726–730.
32. Yates, J. , N. Warner, D. Reisman and B Sugden. 1984. A cis-acting element from the Epstein-Barr viral genome that permits stable replication of recombinant plasmids in latently infected cells. Proc. Natl. Acad. Sci. USA 81, 3806–3810.

What is claimed is:

1. A process for producing an immune response to a papillomavirus antigen in a mammal comprising:

administering to the mammal an HPV-33 papillomavirus peptide selected from the group consisting of E1, E2, E4, E5, E6, E7, L1, L2, and fragments of any of the foregoing peptides, wherein administration results in an immune response.

2. The process of claim 1, comprising administering E1 or a fragment thereof.

3. The process of claim 1, comprising administering E2 or a fragment thereof.

4. The process of claim 1, comprising administering E4 or a fragment thereof.

5. The process of claim 1, comprising administering E5 or a fragment thereof.

6. The process of claim 1, comprising administering E6 or a fragment thereof.

7. The process of claim 1, comprising administering E7 or a fragment thereof.

8. The process of claim 1, comprising administering L1 or a fragment thereof.

9. The process of claim 1, comprising administering L2 or a fragment thereof.

10. The process of claim 2, comprising administering a peptide having a molecular weight of about 72.4 kilodaltons or less.

11. The process of claim 3, comprising administering a peptide having a molecular weight of about 40.2 kilodaltons or less.

12. The process of claim 4, comprising administering a peptide having a molecular weight of about 9.5 kilodaltons or less.

13. The process of claim 5, comprising administering a peptide having a molecular weight of about 9.4 kilodaltons or less.

14. The process of claim 6, comprising administering a peptide having a molecular weight of about 17.6 kilodaltons or less.

15. The process of claim 7, comprising administering a peptide having a molecular weight of about 10.8 kilodaltons or less.

16. The process of claim 8, comprising administering a peptide having a molecular weight of about 55.8 kilodaltons or less.

17. The process of claim 9, comprising administering a peptide having a molecular weight of about 50.5 kilodaltons or less.

18. The process of claim 1, wherein the peptide is produced using recombinant DNA technology.

19. The process of claim 18, wherein the peptide is produced in *E. coli*.

20. A process for obtaining antibodies from a mammal comprising:

administering to a mammal an HPV-33 papillomavirus peptide selected from the group consisting of E1, E2, E4, E5, E6, E7, L1, L2, and fragments of any of the foregoing peptides, wherein administration results in an immune response, and obtaining antibodies from the mammal in which the immune response has occurred.

21. The process of claim 20, wherein obtaining antibodies comprises:

collecting whole blood or serum from the mammal in which the immune response has occurred, separating a soluble fraction from an insoluble fraction of the whole blood or serum, and isolating antibodies from the insoluble or soluble fraction.

22. The process of claim 21, wherein isolating antibodies involves affinity purification.

23. The process of claim 22, wherein affinity purification is performed with E1 or a fragment thereof.

24. The process of claim 22, wherein affinity purification is performed with E2 or a fragment thereof.

25. The process of claim 22, wherein affinity purification is performed with E4 or a fragment thereof.

26. The process of claim 22, wherein affinity purification is performed with E5 or a fragment thereof.

27. The process of claim 22, wherein affinity purification is performed with E6 or a fragment thereof.

28. The process of claim 22, wherein affinity purification is performed with E7 or a fragment thereof.

29. The process of claim 22, wherein affinity purification is performed with L1 or a fragment thereof.

30. The process of claim 22, wherein affinity purification is performed with L2 or a fragment thereof.

* * * * *